United States Patent [19]

Born et al.

[11] 4,347,062

[45] Aug. 31, 1982

[54] COMPLEXES OF HIGH IRON CONTENT SOLUBLE IN ORGANIC MEDIA AND USABLE AS COMBUSTION ADDITIVES IN LIQUID FUELS

[75] Inventors: Maurice Born, Nanterre; Lucienne Briquet; Gabriel de Gaudemaris, both of Rueil-Malmaison, all of France

[73] Assignee: Institut Francais du Petrole, Rueil-Malmaison, France

[21] Appl. No.: 130,307

[22] Filed: Mar. 14, 1980

[30] Foreign Application Priority Data

Mar. 16, 1979 [FR] France .................. 79 06783

[51] Int. Cl.$^3$ ............................................. C10L 1/30
[52] U.S. Cl. .................................. 44/68; 260/429 K; 260/439 R
[58] Field of Search ............... 260/439 R, 429 K; 44/68

[56] References Cited

U.S. PATENT DOCUMENTS 2,279,086  4/1942  Bergstrom .................. 260/448 R
3,085,866  4/1963  Gay et al. .................. 44/57
3,897,470  7/1975  Sias .......................... 260/439 R

FOREIGN PATENT DOCUMENTS 2172797  5/1973  France .

Primary Examiner—Patrick Garvin
Assistant Examiner—Y. Harris-Smith
Attorney, Agent, or Firm—Millen & White

[57] ABSTRACT

A combustion improving additive for liquid fuel consisting essentially of an iron complex soluble in organic media, formed by reacting a sulfonic acid with ferric hydroxide in such proportions as to obtain a ratio of the number of acid gram-equivalents of the sulfonic acid to the number of gram-atoms of the iron in the range from 1/6 to 1/12, said reaction being conducted in the presence of a light aromatic hydrocarbon or a light halogenated aliphatic hydrocarbon having a boiling point from 80° to 230° C. and of an organic liquid containing oxygen, at least partially miscible with water and substantially miscible with hydrocarbons, said complex being obtained in the organic phase of the reaction product.

42 Claims, No Drawings

COMPLEXES OF HIGH IRON CONTENT SOLUBLE IN ORGANIC MEDIA AND USABLE AS COMBUSTION ADDITIVES IN LIQUID FUELS

BACKGROUND OF THE INVENTION

The invention relates to iron complexes soluble in organic media, usable as catalysts in various chemical reactions, and particularly as additives for improving the combustion of liquid fuels. It also concerns the preparation of such complex compounds.

It is known that various iron complexes soluble in organic media are used as combustion adjuvants for liquid fuels, a domain where, among the economical and ecological aims, priority is given to the attempts made to save energy and to reduce pollution. Interest in the improvements which can be brought to the efficiency of these combustion adjuvants is thus fully understood.

The combustion of liquid hydrocarbons, such for example as gas-oils, fuel oils or still kerosine oil, leads, even under the optimum economic conditions, to the emission, to a certain extent, of unburnt solid, liquid or gaseous substances, such as, for example as soot, cracked hydrocarbons, carbon monoxide as well as nitrogen oxides. These unburnt substances have the main disadvantages of lowering the yield of the power generators (fuel oil burners, Diesel engines etc . . . ) due to the loss of combustible material and the formation of deposits (mainly soot) on the heat exchangers, which results in a decrease of the heat transfer coefficient, and leads to the emission of noxious fumes which must be eliminated as much as possible. Generally, an attempt is made to obviate these disadvantages by incorporating in the liquid fuels (gas-oils or fuel-oils, for example) iron, calcium or barium compounds soluble in organic media, for example, having the effect of preventing the emission of smokes or at least of reducing their amount. These compounds, by catalytic effect, produce a more complete combustion of the fuels and, accordingly, reduce the weight of the solid combustion residues.

Various methods for manufacturing such complexes soluble in organic media have already been described, particularly in U.S. Pat. Nos. 3,891,401 and 3,897,470 and in French Pat. No. 2,172,797.

More particularly, in French Pat. No. 2,172,797, iron organic complexes soluble in organic media are prepared by a process wherein an organic (carboxylic) acid or an organometalloidic (sulfuric, sulfonic or phosphoric) acid having from 8 to 30 carbon atoms, is reacted with ferric hydroxide either freshly prepared, or prepared in situ by reaction of a base with a ferric salt. The reaction between the organic or organometalloidic acid and the ferric hydroxide takes place particularly in the presence of a hydrocarbon solvent, such as naphtha. The French Pat. No. 2,172,797 specifically illustrates in its examples the preparation of additives soluble in organic media from various organic or organometalloidic acids (oleic acid, fatty acids of "tall oil," (dinonylphenoxy) phosphoric acid and dodecylbenzene sulfonic acid) and describes, as the resultant products, complexes soluble in organic media wherein the ratio of the number of acid equivalents of the organic or organometalloidic acid to the number of iron atoms has the values of 1/2.9; 1/3 and 1/4.2. These values correspond to relatively low iron ratios with respect to the organic or organometalloidic acid involved.

SUMMARY OF THE INVENTION

It has now been discovered that it is possible to prepare iron complexes soluble in organic media, of increased iron content. As a matter of fact, a process has been invented which makes use of a lower molar proportion of organic binders. This process is particularly advantageous when it is desired to use, as raw materials, alkylbenzene sulfonic acids of relatively high molecular weight, for example, from about 400 to 500, which could not be used when operating under the conditions of the preparation methods of the prior art. As a matter of fact, the operating conditions of the prior art would lead to a solid paste wherefrom the extraction of a complex soluble in organic media is economically impossible.

The compounds of the invention, usable particularly as additives for improving the combustion of liquid fuels, may be defined generally as consisting essentially of complexes, soluble in organic media, formed of at least one sulfonic acid and iron, and in which the ratio R of the number of gram-equivalents of the sulfonic acid to the number of gram-atoms of iron has a value from about 1/6 to about 1/10. The compounds of the invention also include complexes of the same type which are soluble in organic media, but having the ratio R lower than 1/10 and for example, as low as about 1/12.

The sulfonic acid considered in this invention may be an aliphatic, alicyclic or aromatic sulfonic acid but, in most cases, it is an aromatic sulfonic acid, such as an alkylbenzene sulfonic acid, which may be selected not only from the alkylbenzene sulfonic acids containing about 10 to 20 carbon atoms but also (and this is a particular advantage of the invention) from those which contain about 20 to 35 carbon atoms. The latter consist of industrial alkylbenzene sulfonic acids called "heavy alkylbenzenesulfonic acids" from which it was not possible to prepare complexes soluble in organic media, particularly with iron, according to the processes of the prior art.

DETAILED DISCUSSION OF THE INVENTION

The iron complex compounds soluble in organic media according to the invention, wherein the ratio R is from about 1/6 to 1/12, are obtained by a process wherein, as in the prior art, a sulfonic acid is reacted with ferric hydroxide which has been either freshly prepared, or prepared in situ by reaction of a base with a ferric salt, but which differs from the methods of the prior art essentially in that the reaction is conducted in the presence of a solvent system with two elements, comprising:

(a) at least one water-immiscible liquid compound selected from the light aromatic hydrocarbons and the light halogenated aliphatic hydrocarbons, having for example a boiling point from 80° to 230° C., and (b) at least one liquid organic compound including at least one oxygen-containing group and at least partially miscible with an aqueous media, and substantially miscible with a hydrocarbon medium.

(By the phrase, "at least partially miscible with an aqueous medium," it is intended, according to the invention, that the miscibility be at least 10 grams of compound (b) for 100 g of water).

Particular examples of solvent (a) are benzene, toluene, xylenes, mono- and diethylbenzene, mono- and di-isopropylbenzene or trichloroethylene. In most cases toluene and di-isopropylbenzene are used.

In a first embodiment of the process for manufacturing iron complexes soluble in organic media according to the invention, the constituent (b) of the solvent system consists of at least one lower saturated aliphatic mono-alcohol, having for example a boiling point from 65° to 85° C.

As the mono-alcohol (b) there can be used particularly methanol, ethanol, isopropanol or tert-butanol, methanol being preferred.

In the so-formed solvent system, the two constituents (a) and (b) are present in various relative proportions, ranging from 30 to 90% (preferably from 45 to 75%) for the constituent (a), by volume with respect to the total volume of the constituents (a) and (b); the proportion of constituent (b) being of course the complement to 100%, i.e. from 70 to 10% (preferably from 55 to 25%) by volume.

Furthermore, the total amount of the solvent system (a)+(b) may vary within a wide range. Generally, from about 300 to 1,000 cc are used for 100 g of sulfonic acid.

The preparation of complexes soluble in organic media, having the highest iron content, corresponding for example, to a ratio R, as above defined, of about 1/10 and which can be lowered, for example, down to about 1/12, is effected, according to a particularly advantageous embodiment of the invention, by means of a process similar to that described above, but wherein the reaction medium contains a suitable proportion of at least one lower aliphatic carboxylic acid such as for example, as formic acid, acetic acid or propionic acid. Preferably acetic acid is used.

The proportion of carboxylic acid may vary and can be, for example, from 0.1 to 3 moles, preferably from 0.75 to 1.75 moles, per mole of sulfonic acid involved. Up to now it has not been possible to elucidate the mode of action of the lower carboxylic acid on the formation of the iron complex, but now it has become apparent, surprisingly, that the presence of such an acid in the reaction medium results in a substantial increase of the iron amount which can be fixed as complex.

According to another embodiment of the process of preparation of the iron complexes soluble in organic media according to the invention, the oxygen-containing organic liquid (constituent (b)) may also consist of:
an organic compound with alkylene oxide groups complying with the general formula $$R^1-O-(-C_mH_{2m}-O-)_n-R^2$$

wherein $R^1$ is a monovalent aliphatic radical containing, for example, from 1 to 6 carbon atoms or an acyl radical $R^3$ —CO—, where $R^3$ itself is a hydrogen atom or a monovalent aliphatic radical containing, for example, from 1 to 4 carbon atoms, $R^2$ is defined as $R^1$ but may also be a hydrogen atom; m is an integer selected from 2 and 3 and n is an integer from 1 to 4;
a di- or poly-hydroxy hydrocarbon at least partially miscible with water and having a sufficient number of carbon atoms to be miscible with a hydrocarbon medium, such for example as 2-methyl-2,4-pentanediol;
a ketone-alcohol, such for example as 4-methyl-4-hydroxy-2-pentanone (or di-acetone-alcohol); or
a cyclic compound with ether (s) group (s) such as, for example, tetrahydrofuran, dioxane or trioxane.

In most cases organic compounds will be used which comply with the general formula $$R^1-O-(-C_mH_{2m}-O-)_n-R^2,$$

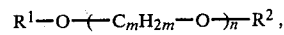

such as above-defined. As specific examples of the latter, there can be described:
alkylene glycol or polyalkylene glycol monoethers, such as for example, as ethylene glycol monomethylether, monoethylether and monoisopropylether, di-ethyleneglycol monomethylether, monoethylether and monobutylether, triethyleneglycol monobutylether;
alkyleneglycol or polyalkyleneglycol diethers such as, for example, ethyleneglycol dimethylether, diethyleneglycol dimethylether, diethyleneglycol diethylether or tetraethyleneglycol dimethylether;
alkyleneglycol or polyalkyleneglycol monocarboxylates, such as ethyleneglycol acetate;
alkyleneglycol or polyalkyleneglycol dicarboxylates such as ethyleneglycol diacetate, diethyleneglycol diacetate, triethyleneglycol diacetate or propyleneglycol diacetate;
alkyleneglycol or polyalkyleneglycol monoethers-monocarboxylates, such as ethyleneglycol acetate-monomethylether, ethyleneglycol acetate-monoethylether, diethyleneglycol acetate-monoethylether, diethyleneglycol acetate-monomethylether, diethyleneglycol acetate-monobutylether or triethyleneglycol acetate-monomethylether.

Among the so-defined oxygen-containing organic compounds, the preferred ones are those having both an excellent miscibility with water, and an excellent miscibility with hydrocarbon media, particularly with the compounds aromatic media. This is the case particularly:
diethyleneglycol monomethylether,
diethyleneglycol monoethylether,
triethyleneglycol monobutylether,
diethyleneglycol dimethylether, and
tetrahydrofuran.

When constituent (b) is selected from the above-defined compounds, the respective proportions of the two constituents (a) and (b) in the solvent system may vary within wide limits; there can be used, for example, from 50 to 95% by volume of constituent (a), and 50 to 5% by volume of constituent (b). Preferred proportions are from 70 to 90% by volume of constituent (a), and 30 to 10% by volume of constituent (b).

Similarly as in the first embodiment, the total volume of the solvent system (a)+(b) may vary within a wide range. Generally, from about 300 to 1,000 cc are used for 100 g of sulfonic acid.

The second embodiment of the manufacturing process of the invention is more particularly applicable in the case where the reaction medium contains a lower aliphatic monocarboxylic acid, such as for example, acetic acid, as provided for in the first embodiment.

However, such an acid will generally be introduced into the reaction medium in a higher proportion, for example, of at least about 3 moles of aliphatic monocarboxylic acid per mole of sulfonic acid.

For effecting the contact between the sulfonic acid and the ferric hydroxide, there can be used, in all the considered cases, freshly precipitated ferric hydroxide, separately prepared, for example, by addition of a base, such as ammonia, sodium hydroxide or potassium hydroxide (for example as an aqueous solution), to a ferric salt, such as ferric chloride, or nitrate in aqueous solution. The so-precipitated ferric hydroxide, after separation and washing, is then introduced, in a suitable proportion, into the reaction mixture. However, in most cases the operation will be performed by forming ferric hydroxide in situ, i.e., in the reaction medium itself, by adding to the latter a suitable proportion of ferric iron, for example, in the form of an aqueous solution of a ferric salt such as the chloride or the nitrate, and then a base such as ammonia, sodium hydroxide, or potassium hydroxide, for example, as an aqueous solution. The ferric salt is generally used in excess, and the addition of the base is advantageously conducted at a temperature not in excess of 40° C. and generally permits bringing the "pseudo-pH" of the reaction medium to a value of from about 3 to 4.

The reaction between the sulfonic acid and the ferric hydroxide is generally effected under vigorous stirring and produces a colloidal mass of gelatinous aspect. The whole mass is then heated, for example at the reflux temperature of the most volatile constituent (generally the oxygen-organic compound), up to the fluidization of the medium. The medium is then allowed to settle and separates into:

an aqueous phase containing, in particular, at least a portion of the oxygen-containing organic solvent involved (constituent (b)) and a portion of the aliphatic monocarboxylic acid optionally introduced in the reaction mixture, and an organic phase containing particularly the desired iron-complex soluble in organic media, dissolved in the light aromatic hydrocarbon solvent or in the light halogenated aliphatic hydrocarbon solvent involved (constituent (a)), optionally associated with a residual fraction of the oxygen-containing organic solvent (constituent (b)).

In some cases, the phase separation may be facilitated by introducing a light aliphatic hydrocarbon solvent (having for example a boiling point from 35° to 70° C.) such as pentane, petroleum ether or hexane, into the medium, this solvent being subsequently removed, for example, by evaporation under reduced pressure, after the phase separation has occurred.

The phase separation may still be facilitated by centrifugation of the medium after the reaction.

After the separation of the phases, the desired complex soluble in organic media may be recovered from the organic phase, for example, by drying, (so as to remove residual water which could be still present in the organic phase), filtration (to remove insoluble impurities, if any), then evaporation of the solvent, for example, under reduced pressure. However, it is also possible, and this is more often the case, to obtain the complex soluble in organic media, according to this invention, as a solution in the separated organic phase. Then only the drying and the filtration thereof is performed.

Finally, to remove the residual acidity of the product, if any, the organic phase may be in every case, subjected to a steam-distillation or a treatment with a base, for example, by addition of ammonia, sodium carbonate or bicarbonate, or even an amine, until a "pseudo-pH" close to 7 is obtained, this finishing treatment being advantageously followed with a filtration.

In their use as combustion adjuvants, the iron complexes soluble in organic media of the present invention may be added to various liquid fuels (gas-oils, fuel-oils) as solid compounds or even as a solution in the organic medium in which they have been obtained. In this case, the starting proportions are generally selected so that the final solution of iron complex has an iron content by weight of about 10%.

The proportion of iron complex soluble in organic media introduced in the liquid fuels may be varied. It is generally from 10 to 150 ppm, preferably from 30 to 100 ppm, calculated as iron weight in proportion to the weight of liquid fuel.

EXAMPLES OF EMBODIMENTS OF THE INVENTION

The following examples illustrate the invention but are not intended in any manner to limit the scope thereof to the practical particular embodiments described therein.

EXAMPLE 1

In a glass Grignard reactor of 2 liters, with a double jacket, there are successively introduced:

81.6 g of synthesized heavy alkylbenzene sulfonic acid (having an equivalent molar mass, taking account a content of 30% by weight of unsulfonated compounds, close to 700 g), i.e. $11.66 \cdot 10^{-2}$ mole of acid;

140 cc of toluene, and 175 cc of methanol.

200.5 cc of an aqueous commercial solution of ferric chloride containing 42% by weight of Fe $Cl_3$ (d=1.45), which corresponds to $75.2 \cdot 10^{-2}$ mole of anhydrous Fe $Cl_3$ or to 42.1 g of iron, is then added.

In one hour there is then added dropwise 200 cc of an aqueous ammonia solution at a 20.88% by weight concentration (d=0.92), under vigorous stirring conditions. There is obtained a colloidal mass of gelatinous aspect.

The whole mass is then heated up to methanol reflux and the heating is maintained for one hour. During this period, the medium progressively fluidizes until there is a complete disappearance of the colloidal mass.

After half an hour of decantation, the aqueous phase is easily separated from the organic phase of a brown-red color. The latter is dried on anhydrous sodium sulfate, filtered, and then evaporated under reduced pressure at 100° C. There is thus recovered 148.4 g of a red-brown solid product, having an iron content of 28.3% by weight, i.e. 42 g of iron. The rate of conversion of inorganic iron to iron soluble in organic media is thus greater than 99%. The ratio (1/R) of the number of iron gram-atoms to the number of sulfonic acid moles in the complex is thus 6.4.

EXAMPLE 2

The same operating conditions as in example 1 are repeated using 77.2 g of another synthesized heavy alkylbenzenesulfonic acid (having an equivalent molecular weight of 663 g) i.e. $11.64 \cdot 10^{-2}$ mole of acid.

There is thus obtained, after drying, filtration and evaporation of the organic phase, 147 g of solid product soluble in organic media containing 41.7 g of iron (i.e. 28.4% by weight). The rate of conversion of inorganic iron to iron soluble in organic media is about 99%. The ratio 1/R is, here also, close to 6.4.

In the following examples 3 to 8, acetic acid has been used as co-reactant whereby the iron content of the prepared complexes soluble in organic media has been further increased.

EXAMPLE 3

Under the same conditions as in examples 1 and 2, there is introduced into the Grignard reactor successively:
- 81.6 g of synthesized heavy alkylbenzenesulfonic acid (the same as in example 1), i.e. 11.66 $10^{-2}$ mole of acid;
- 450 cc of toluene;
- 175 cc of methanol; and
- 12 cc of acetic acid (i.e. 12.24 g or still 20.4 $10^{-2}$ mole).

There is subsequently added 286.5 cc of a commercial aqueous solution of ferric chloride at a 42% by weight concentration of Fe Cl$_3$, which corresponds to 1.074 mole of anhydrous Fe Cl$_3$, or still 60.13 g of iron.

There is thus introduced, under the same conditions as in example 1, 285 cc of an aqueous ammonia solution (d=0.92). A colloidal precipitate is thus obtained.

After heating to reflux for 1 hour and a half, the colloidal precipitate completely disappears.

Then, after half an hour of decantation, the aqueous phase is separated from the organic phase; the latter, of brown-red colour, is then dried and evaporated at 100° C. under reduced pressure.

The analysis of the recovered aqueous phase and of the dry organic product gives the following results:

The iron amount fixed in the additive soluble in organic media (59.4 g, i.e. 1.063 gram-atom) corresponds to 99% of the iron involved at the beginning as ferric chloride. The iron content of the additive is 32.54% by weight.

The amount of acetic acid fixed by the additive (obtained by difference between the amount initially involved and the amount recovered in the aqueous phase) is 11.74 g (i.e. 19.57 $10^{-2}$ mole), which corresponds to about 95.9% of the acetic acid involved at the beginning.

The ratio (1/R) between the number of iron gram-atoms and the number of sulfonic acid equivalents in the complex is here equal to 9.1.

EXAMPLE 4

The operating conditions are the same as in example 3 but with different proportions of the various reactants and ingredients.

There is used:
- 81.6 g of synthesized heavy alkylbenzenesulfonic acid (as in example 1), i.e. 11.66 $10^{-2}$ mole of acid;
- 565 cc of toluene;
- 190 cc of methanol;
- 48.6 cc of acetic acid (i.e. 51 g or 0.85 mole).

There is further added 360 cc of the aqueous ferric chloride solution at a concentration of 42% by weight, which corresponds to 1.337 mole of anhydrous Fe Cl$_3$ or to 74.67 g of iron, and then 360 cc of an aqueous ammonia solution (d=0.92).

In these conditions, after the operations described in example 3, there is obtained 200.0 g of dry additive soluble in organic media, containing 66.24 g of iron (i.e. 1.186 gram-atom), which corresponds to a proportion of fixed iron of 88.7% with respect to the initial iron amount.

The additive soluble in organic media has an iron content of 33.12% by weight.

In the present case, the ratio 1/R has a value of 10.17.

In examples 5 to 8, the operating conditions of example 3 are repeated, except that the acid co-reactant or one of the solvents of the system is changed.

EXAMPLE 5

Acetic acid is replaced with 15 g (12.3 cc) of formic acid.

There is finally obtained 180 g of dry additive soluble in organic media, containing 55.8 g of iron (i.e. 31% by weight). The ratio 1/R in this case is 8.6.

EXAMPLE 6

Methanol is replaced with an equal volume (176 cc) of ethanol.

There is finally obtained 175 g of dry additive soluble in organic media containing 53.7 g of iron (i.e. 30.7% by weight). The ratio 1/R in this case is 8.2.

EXAMPLE 7

Toluene is replaced by the same volume (450 cc) of xylene.

There is obtained 176 g of dry additive soluble in organic media, which contains 53.7 g of iron (30.5% by weight). The ratio 1/R is in this case also close to 8.2.

EXAMPLE 8

Toluene is replaced, this time, by an equal volume of trichloroethylene.

There is obtained 170 g of dry additive soluble in organic media, which contains 52.6 g iron (30.1% by weight). The ratio 1/R, in this case, has a value of about 8.1.

EXAMPLE 9

In a glass reactor of a 2 liter capacity, with a double jacket, provided with a cooler, a stirring system, a thermometer, a device for measuring the pH, and two feeding systems for the reactants, there is introduced successively, at room temperature:
- 81.6 g of synthesized heavy alkylbenzene sulfonic acid (having an equivalent molar mass, taking account of a content of 30% by weight of unsulfonated compounds, close to 700 g), i.e. 11.66 $10^{-2}$ mole of acid;
- 448 cc (387 g) of diisopropylbenzene; and
- 38.5 cc (38 g) of diethyleneglycol monoethylether.

There is subsequently added 423 g of an aqueous commercial ferric chloride solution at a 42% by weight concentration of anhydrous FeCl$_3$ (or containing 42.1 g of iron) and 37 g of glacial acetic acid.

Under vigorous stirring, there is subsequently introduced, dropwise, in two hours and a half, 302 g of an aqueous commercial ammonia solution (d=0.92) while maintaining the temperature of the medium at no more than 40° C.

The progress of the neutralization is followed by means of a coaxial glass/calomel electrode immersed in the reaction medium, the measured "pseudo pH" having to be at most equal to 3.9. The mixture at this stage then takes the aspect of a relatively fluid colloidal paste. The reaction is continued for another hour and, subsequently, after withdrawal of the electrode from the reaction medium, and by means of a heating fluid circulated in the double jacket, the mixture is heated up to reflux (100°-108° C.), at the same time however avoiding the wall temperature of the reactor from becoming higher than 130° C.

This temperature is maintained for 3 hours. During this period of reflux, the reaction medium becomes progressively and completely fluidized. The temperature of the heating fluid is then lowered so that the temperature inside the reactor is about 90° C. (the temperature required for avoiding the precipitation of the ammonium chloride crystals from the aqueous phase).

The stirring is discontinued and the liquid mixture is transferred to an insulated separating funnel, where the organic phase is easily separated in one hour. The lower aqueous phase is discharged and the organic phase is retained.

The residual acidity of the organic phase is then eliminated by addition of sodium bicarbonate, up until of a "pseudo pH" close to 7 is obtained.

Then the product is filtered and there is obtained 560 g of additive as a solution containing 10.6% by weight of iron. This corresponds to a ratio R of the number of sulfonic acid gram-equivalents to the number of iron gram-atoms of about 1:9.1.

EXAMPLE 10

The operating conditions of example 9 are repeated except that diethyleneglycol monoethylether is replaced by the same volume of ethyleneglycol monomethylether. After boiling and decantation, there is obtained a combustion additive as a solution having an iron content of 10.4% by weight, which corresponds to a value of the ratio R close to 1:9.

EXAMPLE 11

The operating conditions of example 9 are repeated except that diethyleneglycol monoethylether is replaced by 50 cc of diethyleneglycol dimethylether. After boiling and partial cooling of the reaction mixture, 200 cc of hexane are added to facilitate the decantation.

After separation of the phases and treatment of the organic phase as described in example 9, hexane is evaporated under reduced pressure conditions and the combustion additive is recovered as a solution having an iron content of 10.9% by weight. The ratio R is then at a value of 1:9.4.

EXAMPLES 12-14

The operating conditions of example 9 are repeated except that diethyleneglycol monoethylether is replaced respectively with 40 cc of ethyleneglycol monoacetate (Ex. 12), ethyleneglycol diacetate (Ex. 13) and ethyleneglycol monoacetate-monoethylether (Ex. 14).

As in example 11, after heating to reflux of the reaction mixture followed with a partial cooling, 200 cc of hexane are added to facilitate the decantation.

After evaporation of the hexane, there are obtained three combustion additives as solutions having respective iron contents of 10.6, 8.3 and 10.4% by weight, which corresponds to respective values of the ratio R of about 1:9.2, 1:6.2 and 1:8.9.

EXAMPLE 15

The operating conditions of example 9 are repeated except that diethyleneglycol monoethylether is replaced by 45 cc of diacetone alcohol.

After boiling and decantation, the organic phase, separated and treated as in example 11, forms the desired combustion additive. It appears as a solution having an iron content of 10.3% by weight, i.e. a ratio R of about 1:8.8.

EXAMPLE 16

The operating conditions of example 9, are repeated except that diethyleneglycol monoethylether is replaced by 40 cc of tetrahydrofuran.

After heating to reflux, decantation and separation of the organic phase in the same manner as in example 11, the combustion additive is recovered as a solution having an iron content of 11.1% by weight, i.e. a ratio R of about 1:9.7.

The capacity of the additives of the invention to reduce the rate of emission of solid particles in the combustion has been shown in the following tests.

TEST 1

The additive prepared in example 3 is used in a series of tests conducted with 4 different fuel-oils (each having a viscosity of 20 centistokes at 120° C.) referenced A, B, C and D.

The additive is introduced in each fuel oil at a concentration corresponding to 50 ppm by weight of iron (1.343 g of additive is introduced per 10 kg of fuel-oil).

The 4 fuel-oils including their additives have been used to feed a burner. They were mechanically sprayed under a pressure of 29 bars. The feeding rate of fuel oil was 90 Kg/h. The temperature at the air input was 20° C.

The same test was conducted with fuel-oils without additives (blank tests).

In each test, there was determined the blackening index by weight according to the standard NF X 43-003. It concerns the gravimetric content of solid particles corresponding to 1 thermal unit evolved (it is expressed in mg per thermal unit).

In the following Table, the obtained results are reported for fuels without additives and then for fuels with additives; the efficiency of the additive is also indicated, it corresponds to the relative lowering of the blackening index by weight (in relation with the value of the blank test).

| FUEL | BLACKENING INDEX BY WEIGHT (mg/th.u) | | EFFICIENCY (%) |
|---|---|---|---|
| | BLANK TEST | ADDITIVE OF EXAMPLE 3 | |
| Fuel A | 554 | 360 | 35 |
| Fuel B | 379 | 230 | 39.3 |
| Fuel C | 228 | 125 | 45.2 |
| Fuel D | 84 | 31 | 63 |

TEST 2

The additive prepared in example 9 is used with a heavy fuel oil having a viscosity of 12.5 centistokes at 140° C.

The additive is introduced into the fuel-oil at concentrations corresponding to 50 and 100 ppm by weight of iron: 4.717 g and 9.434 g of a 10.6% by weight iron solution is introduced per 10 Kg of fuel-oil.

Each fuel-oil with an additive is fed to a burner. It is mechanically sprayed at a feeding rate of 130 Kg/h. The inlet temperature of air is 25° C. with a 20% excess of air.

The same test has been performed with the same fuel-oil without additive (blank test).

For each test, the blackening index by weight according to the standard NF X 43-003 has been determined. It corresponds to the gravimetric content of solid particles corresponding to one evolved thermal unit (it is expressed in mg/th.u).

The results obtained for the fuel without additive and then for the fuel with additive are reported below together with the efficiency of the additive which corresponds to the relative lowering of the blackening index by weight (as compared to the value of the blank test).

| IRON CONCENTRATION (p.p.m) | BLACKENING INDEX BY WEIGHT (mg/th.u) | EFFICIENCY (%) |
|---|---|---|
| 0* | 650 | — |
| 50 | 410 | 37 |
| 100 | 350 | 46 |

*Blank test.

The results of the tests 1 and 2 show that the additives prepared according to this invention, having a high iron content, improve the combustion of a heavy fuel to a quite satisfactory extent.

What is claimed is:

1. An iron complex soluble in hydrocarbon fuels, said complex being formed from at least one sulfonic acid and ferric iron; wherein the ratio R of the number of acid gram-equivalents of said sulfonic acid to the number of gram-atoms of iron in said complex is from about 1/6 to 1/12.

2. A complex according to claim 1, wherein the sulfonic acid is an alkylbenzene sulfonic acid containing from 10 to 35 carbon atoms.

3. A complex according to claim 2, wherein said sulfonic acid contains from 20 to 35 carbon atoms.

4. A process for manufacturing an iron complex according to claim 1, said process comprising the steps of:
heating at least one sulfonic acid with sufficient moist ferric hydroxide to obtain said value of said ratio R, in a solvent system comprising:
(a) at least one water-immiscible organic liquid, selected from light aromatic hydrocarbons and light halogenated aliphatic hydrocarbons having a boiling point from 80° C. to 230° C., and
(b) at least one organic liquid having at least one oxygen-containing group and having at least partial miscibility with water and substantial miscibility with hydrocarbons; and
separating the resultant aqueous phase, and recovering the resultant organic phase containing said iron complex.

5. A process according to claim 4, wherein said liquid (b) is a lower saturated aliphatic mono-alcohol having a boiling point from 65° to 85° C.

6. A process according to claim 5, wherein said mono-alcohol is methanol.

7. A process according to claim 5, wherein said liquid (a) amounts to 30 to 90% by volume and said liquid (b) amounts to 70 to 10% by volume of the total solvent system.

8. A process according to claim 7, wherein the amounts of said liquid (a) and said liquid (b) are from 45 to 75% by volume for said liquid (a) and from 55 to 25% by volume for said liquid (b).

9. A process according to claim 4, wherein said contacting is effected in the presence in the reaction medium of a lower aliphatic monocarboxylic acid, in a proportion of about 0.1 to 3 moles per mole of sulfonic acid.

10. A process according to claim 9, wherein said lower aliphatic monocarboxylic acid is acetic acid.

11. A process according to claim 4, wherein said liquid (b) is an organic compound containing at least one alkylene oxide group and having the formula:

wherein $R^1$ is a monovalent aliphatic radical having from 1 to 6 carbon atoms or an acyl radical $R^3$—CO—, in which $R^3$ is a hydrogen atom or a monovalent aliphatic radical having from 1 to 4 carbon atoms; $R^2$ is the same as $R^1$ or is a hydrogen atom; m is 2 or 3 and n is an integer from 1 to 4.

12. A process according to claim 11 wherein said organic compound is selected from ethyleneglycol monomethylether, monoethylether and monoisopropylether, diethyleneglycol monomethylether, monoethylether and monobutylether, triethyleneglycol monobutylether, ethyleneglycol dimethylether, diethyleneglycol dimethylether and diethylether, tetraethyleneglycol dimethylether, ethyleneglycol acetate; ethyleneglycol, diethyleneglycol, triethyleneglycol and propyleneglycol diacetates, ethyleneglycol acetate-monomethylether and acetate monoethylether, diethyleneglycol acetate-monomethylether, acetate-monoethylether and acetatemonobutylether and triethyleneglycol acetate-monomethylether.

13. A process according to claim 4, wherein said liquid (b) is a di- or polyhydroxy hydrocarbon compound having a number of carbon atoms sufficient for being miscible with hydrocarbons.

14. A process according to claim 4 wherein said liquid (b) is a ketone-alcohol having a number of carbon atoms sufficient to be miscible with hydrocarbons.

15. A process according to claim 4, wherein said liquid (b) consists of a cyclic hydrocarbon compound having at least one ether group in the cycle.

16. A process according to claim 11, wherein said liquid (b) is selected from diethyleneglycol monomethylether, diethyleneglycol monoethylether, triethyleneglycol monobutylether, diethyleneglycol dimethylether and tetrahydrofuran.

17. A process according to claim 11, wherein said liquid (a) amounts to 50 to 95% by volume and said liquid (b) to 50 to 5% by volume of the total amount of the solvent system.

18. A process according to claim 17 wherein the respective proportions are 70 to 90% by volume for said liquid (a) and from 30 to 10% by volume for said liquid (b).

19. A process according to claim 11, wherein the reaction medium contains a lower aliphatic monocarboxylic acid, in a proportion of at least 3 moles per mole of sulfonic acid.

20. A process according to claim 19, wherein said lower aliphatic monocarboxylic acid is acetic acid.

21. A process according to claim 4, wherein said liquid (a) is selected from toluene and diisopropylbenzene.

22. A process according to claims 4, wherein the total volume of the solvent system is from 300 to 1,000 cc per 100 g of sulfonic acid.

23. A process according to claim 4, wherein the reaction between said sulfonic acid and said ferric hydroxide is conducted at the reflux temperature of the more volatile constituent of said solvent system.

24. A process according to claim 4, further comprising the addition of a light aliphatic hydrocarbon solvent having a boiling point from 35° to 70° C., for facilitating the separation of the aqueous phase from the organic phase, said solvent being subsequently removed from the organic phase.

25. A process according to claim 4, further comprising the reaction medium centrifuging to facilitate the separation of the aqueous phase from the organic phase.

26. A process according to claim 4, further comprising contacting said recovered organic phase with a basic compound, to eliminate its residual acidity.

27. A process according to claim 4, further comprising subjecting said recovered organic phase to a steam distillation, to eliminate therefrom the residual acidity.

28. A solution in an organic medium of an iron complex, produced by the process of claim 4.

29. An iron complex solution according to claim 28, wherein said solution contains about 10% by weight of iron.

30. A process according to claim 4, further comprising evaporating the solvent from said recovered organic phase and recovering the resultant iron complex as a solid.

31. A solution comprising a complex according to claim 1 dissolved in an organic medium.

32. A solution according to claim 31, wherein said solution contains about 10% of iron.

33. A liquid fuel composition, comprising a liquid hydrocarbon fuel oil and an amount dissolved therein sufficient to improve the combustion characteristics of said fuel oil of an iron complex solution according to claim 31.

34. A liquid fuel composition according to claim 33, wherein the proportion of said iron complex corresponds to an iron concentration of from 10 to 150 ppm by weight.

35. A liquid fuel composition according to claim 34, wherein said proportion of said iron complex corresponds to an iron concentration of from 30 to 100 ppm by weight.

36. A complex according to claim 1, wherein said complex is in the dry state.

37. A liquid fuel composition comprising a liquid hydrocarbon fuel oil and an amount dissolved therein sufficient to improve the combustion characteristics of said fuel oil of a iron complex formed from at least one sulfonic acid and ferric iron; wherein the ratio R of the number of acid gram-equivalents of said sulfonic acid to the number of gram-atoms of iron in said complex is from about 1/6 to 1/12.

38. A liquid fuel composition according to claim 37, wherein the amount of said complex in said composition corresponds to a content of 10–150 ppm by weight of iron.

39. A method for improving the combustion and reducing the soot producing characteristics of a fuel oil, which comprises dispersing in said fuel oil an amount effective to improve combustion and reduce soot upon burning of an iron complex according to claim 1.

40. A method according to claim 39, wherein said effective amount of said iron complex corresponds to an iron concentration of 10–150 ppm by weight.

41. An iron complex produced by the process of claim 30.

42. A complex according to claim 1, wherein said ratio R is from about 1/10 to 1/12.

* * * * *